US012390336B2

(12) United States Patent
Wu et al.

(10) Patent No.: US 12,390,336 B2
(45) Date of Patent: Aug. 19, 2025

(54) ARTIFICIAL VERTEBRAL BODY

(71) Applicant: Beijing Naton Medical Technology Holdings Co., Ltd., Beijing (CN)

(72) Inventors: Haiyuan Wu, Beijing (CN); Shufu Xu, Beijing (CN); Xuedong Zhang, Beijing (CN); Xun Zhang, Beijing (CN); Chao Zhen, Beijing (CN); Yalong Dong, Beijing (CN); Xiang Dong, Beijing (CN)

(73) Assignee: BEIJING NATON MEDICAL TECHNOLOGY HOLDINGS CO., LTD., Beijing (CN)

( * ) Notice: Subject to any disclaimer, the term of this patent is extended or adjusted under 35 U.S.C. 154(b) by 0 days.

(21) Appl. No.: 18/291,105

(22) PCT Filed: Jul. 21, 2022

(86) PCT No.: PCT/CN2022/107155
§ 371 (c)(1),
(2) Date: Jan. 22, 2024

(87) PCT Pub. No.: WO2023/124032
PCT Pub. Date: Jul. 6, 2023

(65) Prior Publication Data
US 2025/0099257 A1  Mar. 27, 2025

(30) Foreign Application Priority Data

Dec. 31, 2021 (CN) .......................... 202111660565.9

(51) Int. Cl.
*A61F 2/44* (2006.01)
*A61F 2/30* (2006.01)
(52) U.S. Cl.
CPC ...... *A61F 2/44* (2013.01); *A61F 2002/30405* (2013.01)

(58) Field of Classification Search
CPC ................... A61F 2/44; A61F 2/30767; A61F 2002/30405; A61F 2002/30492;
(Continued)

(56) References Cited

U.S. PATENT DOCUMENTS 5,458,641 A * 10/1995 Ramirez Jimenez ..... A61F 2/44
606/247
6,086,613 A * 7/2000 Camino ................ A61F 2/4465
623/17.16

(Continued)

FOREIGN PATENT DOCUMENTS

CN           114392016 A       4/2022

OTHER PUBLICATIONS

International Search Report issued in International Application No. PCT/CN2022/107155 mailed on Oct. 20, 2022 (7 pages).
(Continued)

*Primary Examiner* — Henry Y Liu
(74) *Attorney, Agent, or Firm* — Osha Bergman Watanabe & Burton LLP

(57) ABSTRACT

An artificial vertebral body includes a housing, a rotating body and a support member; an inner peripheral surface of the housing is provided with a first cooperating portion. The rotating body is rotatably disposed in the housing, an outer peripheral surface of the rotating body being provided with a second cooperating portion; the first cooperating portion can cooperate with the second cooperating part to restrict the rotation body to only rotate clockwise or counterclockwise; the support member passes through the rotating body and is screwed together with the rotating body; and the rotating body can rotate relative to the housing to drive the support member to move along the axial direction of the rotating body.

11 Claims, 6 Drawing Sheets

(58) Field of Classification Search
CPC .. A61F 2002/30522; A61F 2002/30523; A61F 2002/30537; A61F 2002/30556; A61F 2002/30571; A61F 2002/30904; A61F 2002/4638; A61F 2002/30494; A61F 2002/30565
USPC .......................................................... 384/91
See application file for complete search history.

(56) References Cited

U.S. PATENT DOCUMENTS

| | | | | |
|---|---|---|---|---|
| 7,934,909 | B2* | 5/2011 | Nuesser | A61M 60/82 |
| | | | | 384/114 |
| 10,639,165 | B2* | 5/2020 | Suh | A61F 2/441 |
| 10,687,960 | B2* | 6/2020 | Xiao | A61L 27/32 |
| 2002/0138142 | A1* | 9/2002 | Castro | A61F 2/4465 |
| | | | | 623/17.11 |
| 2003/0191531 | A1* | 10/2003 | Berry | A61F 2/4455 |
| | | | | 623/17.11 |
| 2003/0199980 | A1* | 10/2003 | Siedler | A61F 2/44 |
| | | | | 606/247 |
| 2006/0116770 | A1* | 6/2006 | White | A61F 2/44 |
| | | | | 623/17.16 |
| 2007/0255427 | A1* | 11/2007 | Kloos | A61F 2/6607 |
| | | | | 623/53 |
| 2019/0029841 | A1* | 1/2019 | Suh | A61F 2/441 |
| 2019/0029842 | A1* | 1/2019 | Xiao | A61L 27/56 |

OTHER PUBLICATIONS

Written Opinon issued in International Application No. PCT/CN2022/107155 mailed on Oct. 20, 2022 (5 pages).

* cited by examiner

ARTIFICIAL VERTEBRAL BODY

CROSS-REFERENCE TO RELATED APPLICATION

This application is a National Stage Application of International Application No. PCT/CN2022/107155 filed on Jul. 21, 2022, which claims priority to and benefits of Chinese Patent Application Serial No. 202111660565.9 filed in China on Dec. 31, 2021, the entire content of which is incorporated herein by reference.

FIELD

The present disclosure relates to a field of medical instruments, in particular to an artificial vertebral body.

BACKGROUND

Artificial vertebral bodies are used to treat diseases such as vertebral burst fractures, kyphosis deformity and spinal tumors. During surgery, the damaged or diseased vertebral bodies of patients need to be removed, and after removal, vertebral body substitutes are used for transplantation to maintain normal spinal load and physiological curvature.

In the related art, the adjustment of artificial vertebral bodies is inconvenient, the structure thereof is unstable, and endplates thereof are prone to sinking during use.

SUMMARY

An artificial vertebral body according to embodiments of the present disclosure includes: a housing including a first matching portion on an inner circumferential surface of the housing; a rotating body rotatably arranged inside the housing and including a second matching portion on an outer circumferential surface of the rotating body, wherein the first matching portion is fitted with the second matching portion to limit the rotating body to only clockwise or counterclockwise rotation; and a support running through the rotating body and screwed with the rotating body, wherein the rotating body is rotatable relative to the housing to drive the support member to move along an axial direction of the rotating body.

DETAILED DESCRIPTION

Embodiments of the present disclosure will be described in detail, examples of which are illustrated in the accompanying drawings. The embodiments described below with reference to the accompanying drawings are exemplary and are intended to explain the present disclosure rather than limit the present disclosure.

In the related art, there are two types of artificial vertebral bodies: titanium cages and expandable artificial vertebral bodies. The titanium cages have the following drawbacks: the titanium cages need to be cut according to actual heights during surgery, and height matching is poor. Moreover, the titanium cages are easy to collapse, and even if the titanium cages are mounted with upper and lower end covers, other fixation means such as screws are still required, making the operation cumbersome.

The expandable artificial vertebral bodies have no anti-retreat mechanism, and they can achieve stable expansion in static conditions, but endplates may sink in vibration conditions. In addition, a locking mechanism may be mounted in an expandable artificial vertebral body, that is, a screw directly presses and props up an inner core (i.e., a support member in embodiments of the present disclosure). This structure has the following drawbacks: due to the need for screw locking, the expandable body must have a certain thickness, which leads to a smaller internal bone grafting window structure and occupies height space of the vertebral body. Moreover, since the screw directly presses the vertebral body and props up the inner core, the locking effect is not stable, the screw is prone to loosening and the endplate is prone to sinking.

An artificial vertebral body according to embodiments of the present disclosure will be described with reference to FIGS. 1 to 12.

As shown in FIGS. 1-5, the artificial vertebral body according to embodiments of the present disclosure includes a housing 3, a rotating body 4 and a support member 1.

Figure 8:
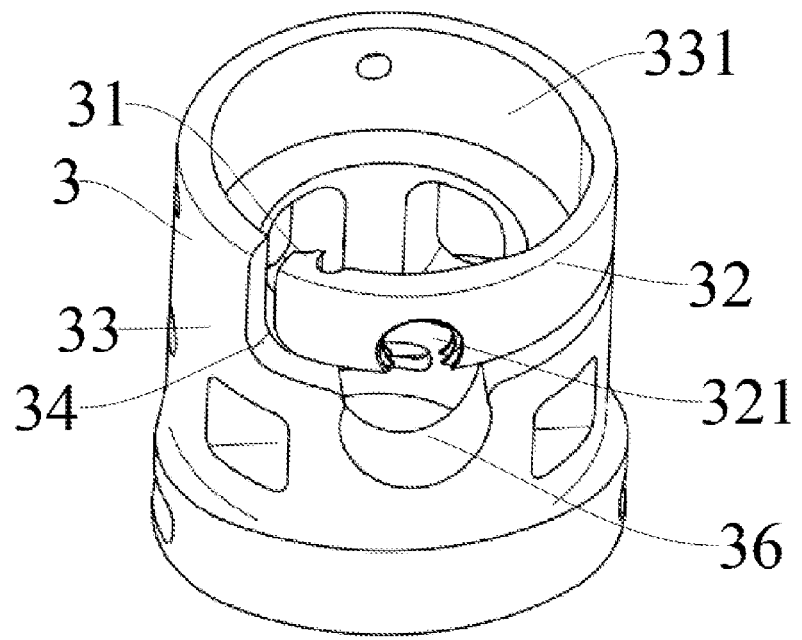
FIG. 8 is a schematic view of the housing of the artificial vertebral body according to the first embodiment of the present disclosure.
Figure 9:
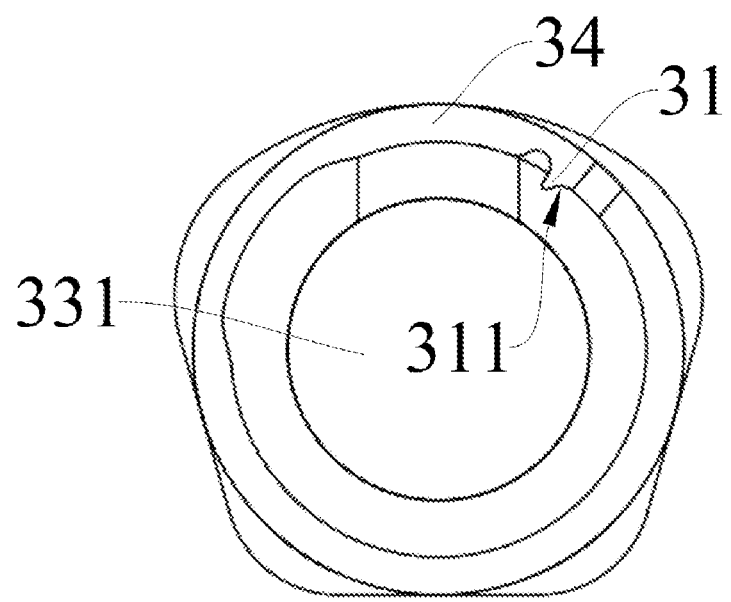
FIG. 9 is a top view of the housing of the artificial vertebral body according to the first embodiment of the present disclosure.

The housing 3 has a first matching portion 31 on its inner circumferential surface. Specifically, as shown in FIGS. 8 and 9, the housing 3 includes the first matching portion 31 on an inner circumferential surface of an upper end of the housing.

The rotating body 4 is rotatably arranged in the housing 3, and the rotating body 4 has a second matching portion 41 on its outer circumferential surface. The first matching portion 31 can be fitted with the second matching portion 41, to limit the rotating body 4 to only clockwise or counterclockwise rotation. Specifically, as shown in FIGS. 4-7, the rotating body 4 is rotatably arranged inside the upper end of the housing 3. The rotating body 4 includes a first portion 43 and a second portion 44 connected to each other, and an outer circumferential surface of the first portion 43 is provided with the second matching portion 41 which can be fitted with the first matching portion 31. Since the first matching portion 31 is fitted with the second matching portion 41, the rotating body 4 can rotate clockwise but not counterclockwise, or the rotating body 4 can rotate counterclockwise but not clockwise.

Figure 1:
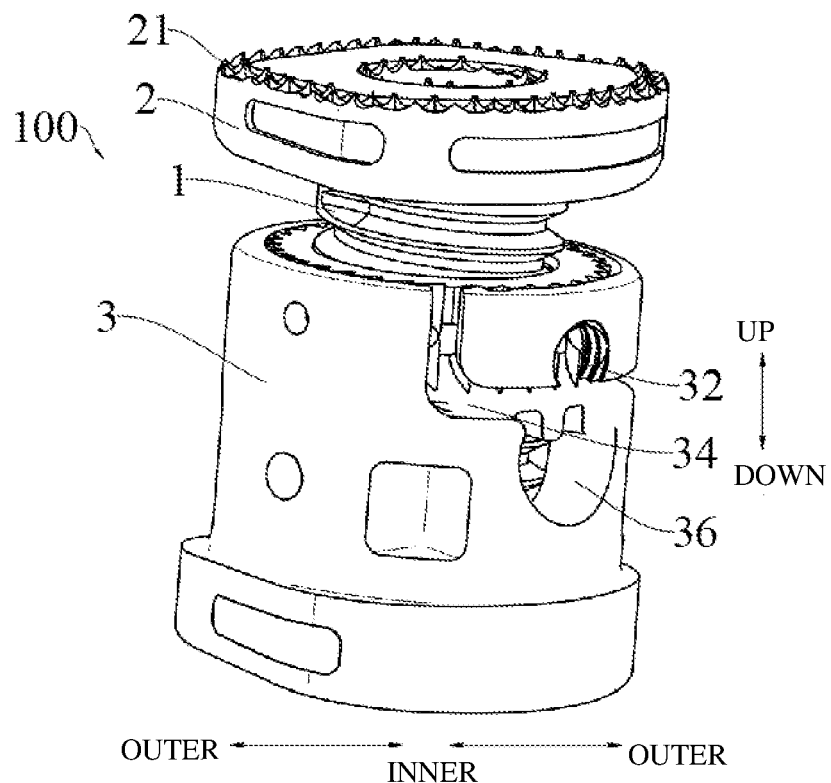
FIG. 1 is a schematic view of an artificial vertebral body according to a first embodiment of the present disclosure.
Figure 2:
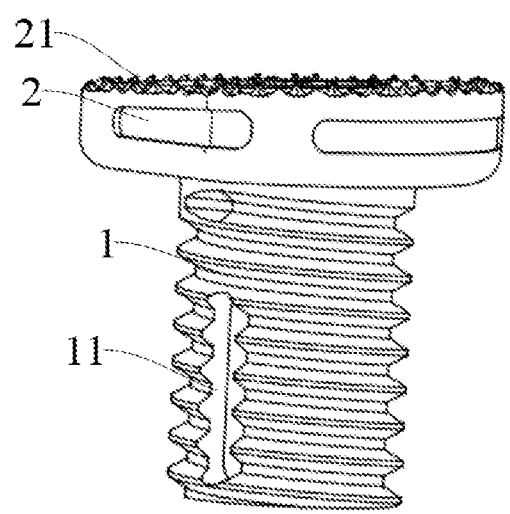
FIG. 2 is a schematic view of a support member and an endplate of the artificial vertebral body according to the first embodiment of the present disclosure.
Figure 3:
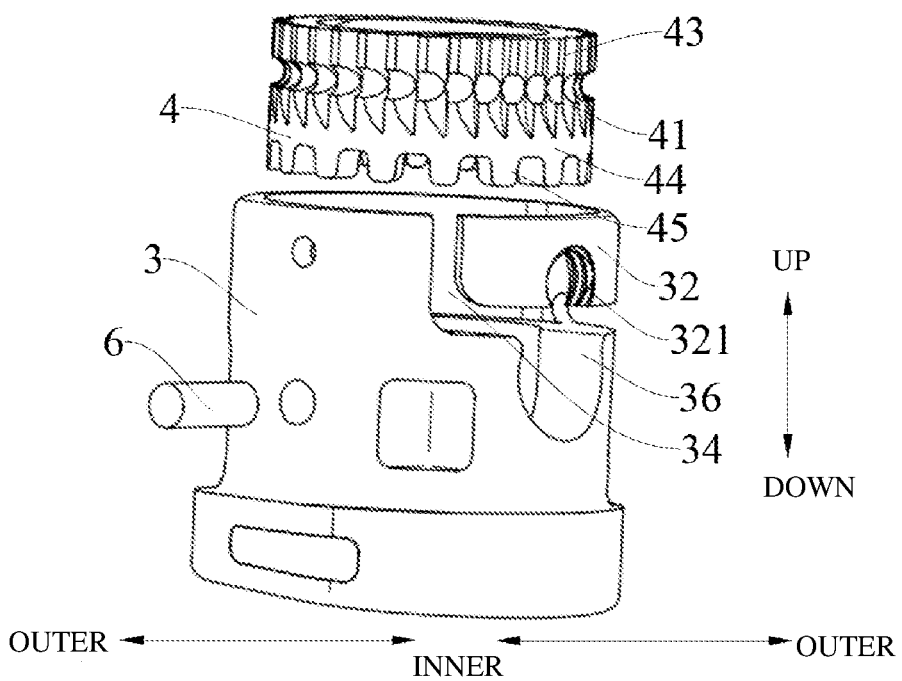
FIG. 3 is an exploded view of a rotating body and a housing of the artificial vertebral body according to the first embodiment of the present disclosure.
Figure 4:
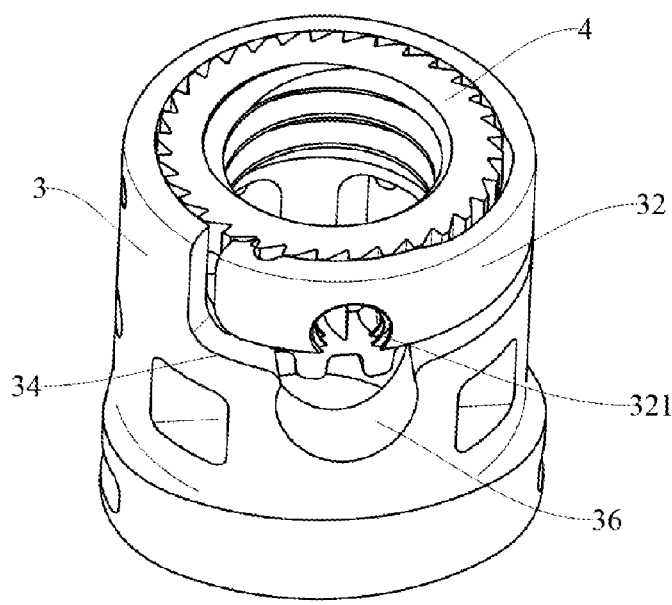
FIG. 4 is an assembly view of the rotating body and the housing of the artificial vertebral body according to the first embodiment of the present disclosure.
Figure 5:
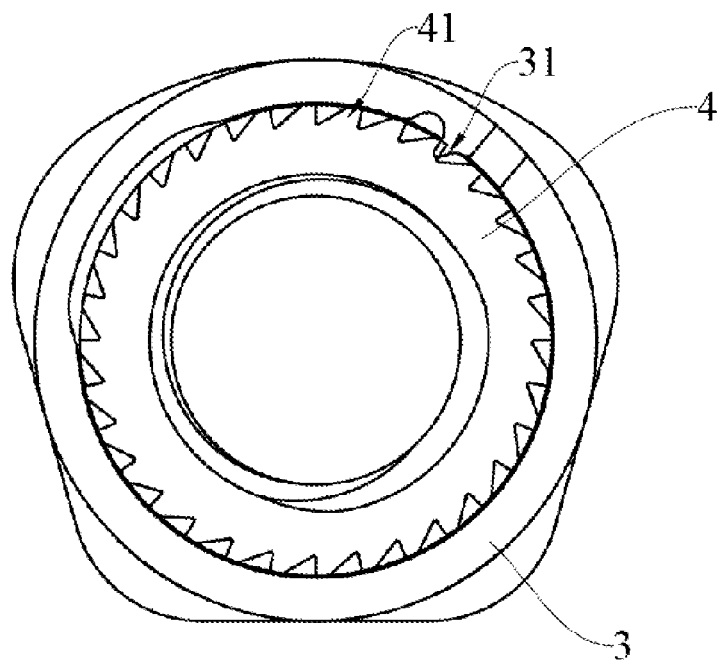
FIG. 5 is a top view of the rotating body and the housing of the artificial vertebral body according to the first embodiment of the present disclosure.
Figure 6:
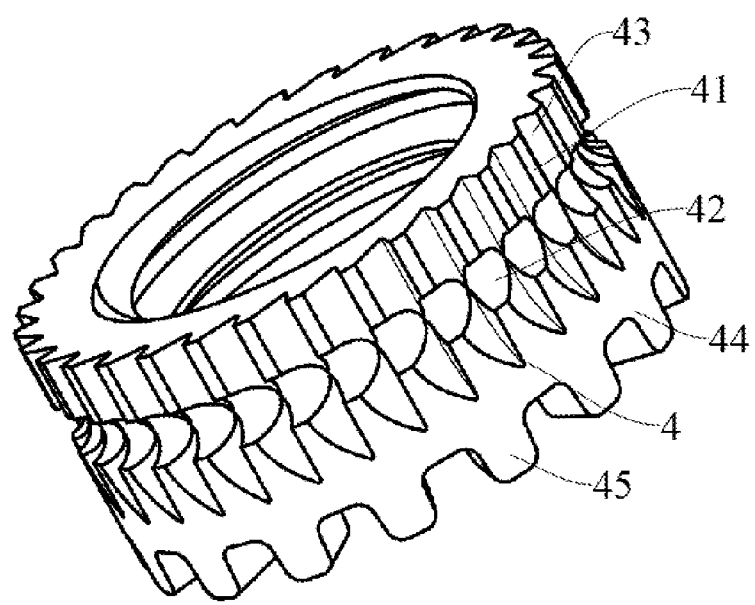
FIG. 6 is a schematic view of the rotating body of the artificial vertebral body according to the first embodiment of the present disclosure.
Figure 7:
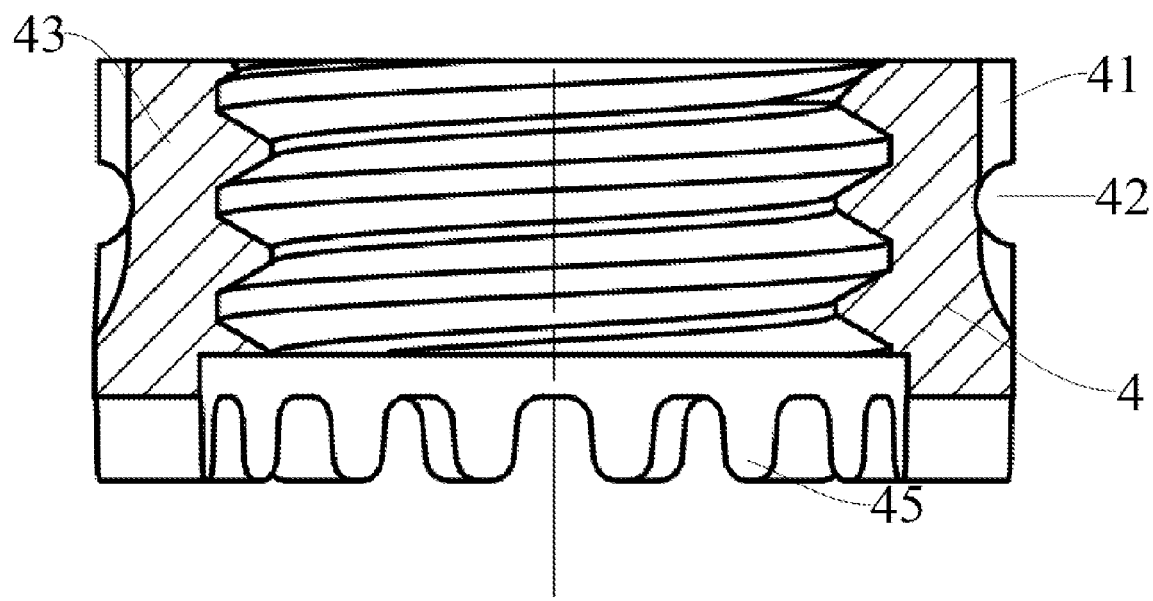
FIG. 7 is a sectional view of the rotating body of the artificial vertebral body according to the first embodiment of the present disclosure.

The support member 1 runs through the rotating body 4 and is screwed with the rotating body 4. The rotating body 4 can rotate relative to the housing 3 to drive the support member 1 to move along an axial direction of the rotating body 4 (an up-down direction as shown in FIG. 1). Specifically, as shown in FIGS. 1-3, the support member 1 runs through the rotating body 4, and a lower end of the support member 1 is inside the housing 3. The support member 1 has external threads on its outer circumferential side, and the rotating body 4 has internal threads on its inner circumferential side. In such a way, the support member 1 is driven to move upward by the clockwise rotation of the rotating body 4; after the artificial vertebral body 100 is expanded, the first matching portion 31 and the second matching portion 41 can realize self-locking of the expansion mechanism to prevent the rotating body 4 from rotating counterclockwise and to stably maintain the height of the support member 1. Alternatively, as shown in FIGS. 4 and 5, the rotating body 4 rotates counterclockwise to drive the support member 1 to move upward; after the artificial vertebral body 100 is expanded, the first matching portion 31 and the second matching portion 41 can realize self-locking of the expansion mechanism to prevent the rotating body 4 from rotating clockwise and to stably maintain the height of the support member 1.

For the artificial vertebral body 100 according to the embodiments of the present disclosure, with the arrangement of the rotating body 4, the first matching portion 31 and the second matching portion 41, the rotating body 4 can drive the support member 1 to move up and down, so that the artificial vertebral body 100 is expanded; the first matching portion 31 and the second matching portion 41 can realize the self-locking of the expansion mechanism of the artificial vertebral body 100, to keep the height of the artificial vertebral body 100 stable; and since the first matching portion 31 is on the inner circumferential surface of the housing and the second matching portion 41 is on the rotating body 4, there is no specific requirement for the thickness of an outer wall of the housing 3, and the arrangement of the first matching portion 31 and the second matching portion 41 will not affect the space for bone grafting.

In the embodiments, the rotating body 4 includes a plurality of operation teeth 45 at an end of the rotating body facing an interior of the housing 3. The plurality of operation teeth 45 extend along a circumferential direction of the rotating body 4 and are evenly spaced apart from each other along the circumferential direction of the rotating body 4. The housing 3 includes an operation hole 36, and some of the operation teeth 45 are corresponding to the operation hole 36 in a radial direction of the rotating body 4 (an inner-outer direction as shown in FIG. 1). Specifically, as shown in FIGS. 2 and 3, a lower end face of the second portion 44 is provided with the plurality of operation teeth 45, which are arranged at equal intervals along the circumferential direction of the rotating body 4. The housing 3 includes the operation hole 36 that penetrates the housing 3 and is corresponding to the operation teeth 45 in the inner-outer direction. A rotation handle 5 can be used to pass through the operation hole 36 and cooperate with the operation teeth 45 of the second portion 44, so that the rotating body 4 can be driven to rotate in the housing 3 by rotating the rotation handle 5. It can be understood that an end of the rotation handle 5 connected to the operation hole 36 has a gear structure that can mesh with the operation teeth 45, so that the rotation handle 5 can be rotated to drive the rotating body 4 to rotate. The operation handle 5 and the gear structure are known in the art and will not be described here.

In some embodiments, the housing 3 includes an elastic portion 32, which is corresponding to the rotating body 4 in the radial direction (inner-outer direction as shown in FIG. 1) of the rotating body 4. The first matching portion 31 is on an inner side of the elastic portion 32, so that the elastic portion 32 can drive the first matching portion 31 to separate from the second matching portion 41.

Specifically, as shown in FIGS. 3-12, the elastic portion 32 has an ability of elastic deformation. The elastic portion 32 is at the upper end of the housing 3 and corresponding to the rotating body 4 in the inner-outer direction, and the first matching portion 31 is located at an inner circumferential side of the elastic portion 32. When the height of the support member 1 needs to be reduced, the elastic portion 32 is pulled to move outward in the inner-outer direction to drive the first matching portion 31 to move outward; or the elastic portion 32 is pulled to move upward in the up-down direction to drive the first matching portion 31 to move upward; or the elastic portion 32 is pulled to move downward in the up-down direction to drive the first matching portion 31 to move downward. As a result, the first matching portion 31 is separated from the second matching portion 41 on the rotating body 4, to realize unlocking between the first matching portion 31 and the second matching portion 41, and hence allow the rotating body 4 to reverse to lower the position of the support member 1. When the position of the support member 1 is adjusted to an appropriate position, the elastic portion 32 can be released. Since the elastic portion 32 has the ability of elastic deformation, the elastic portion 32 can drive the first matching portion 31 to automatically fit with the second matching portion 41 to prevent the support member 1 from sinking.

Figure 11:
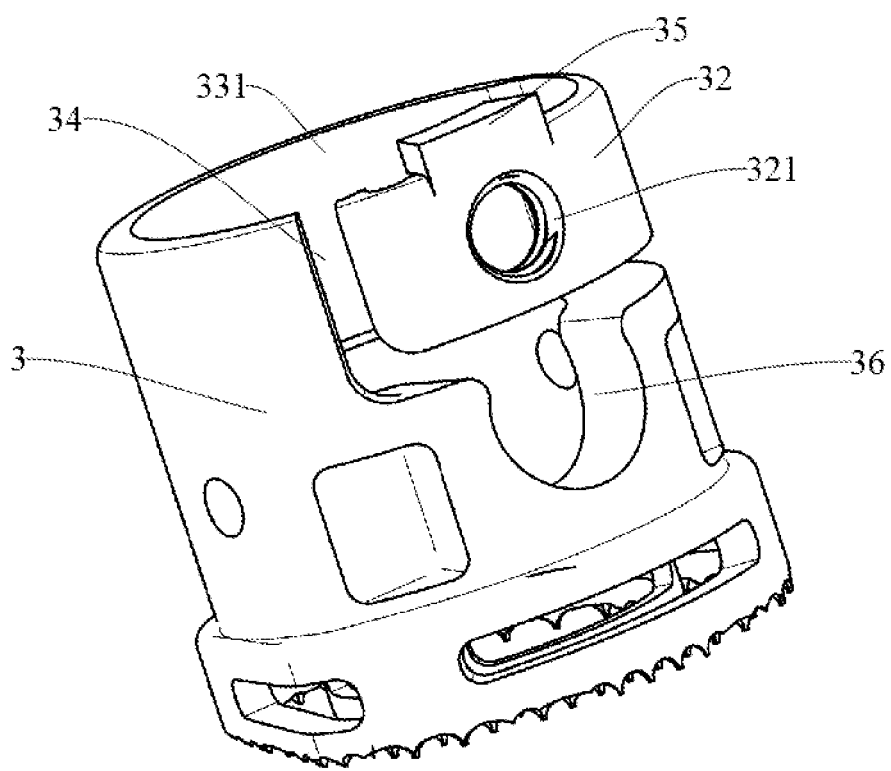
FIG. 11 is a schematic view of the housing of the artificial vertebral body according to the second embodiment of the present disclosure.
Figure 12:
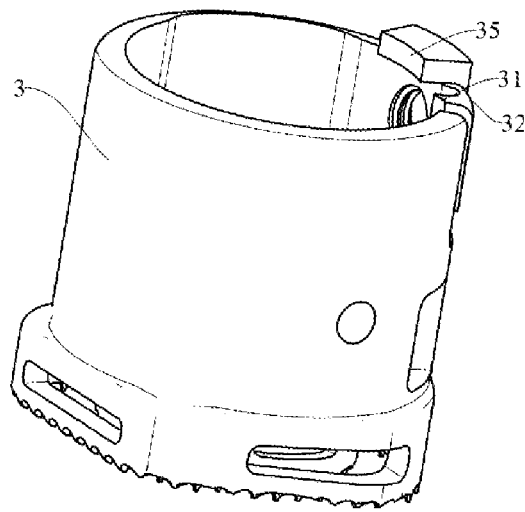
FIG. 12 is a schematic view of the housing of the artificial vertebral body according to the second embodiment of the present disclosure.

In some embodiments, the housing 3 includes a base body 33 and the elastic portion 32, the base body has a cavity 331, and the rotating body 4 is rotatably arranged in the cavity 331. An end of the base body 33 adjacent to the rotating body 4 includes a notch 34, and the elastic portion 32 is arranged in the notch 34. The elastic portion 32 extends along a circumferential direction of the housing 3, and an end of the elastic portion 32 in the extension direction is connected to the housing 3. Specifically, as shown in FIGS. 8, 11 and 12, the base body 33 is a sleeve without a top surface, an inner circumferential surface of the sleeve defines the cavity 331, and the rotating body 4 is rotatably arranged in the cavity 331. A side surface of an upper end of the base body 33 is provided with the notch 34 running through the base body 33 in the inner-outer direction, the elastic portion 32 is arranged in the notch 34, and a first side of the elastic portion 32 is connected to the notch 34. An upper end face of the elastic portion 32 is flush with the base body 33. A bottom surface of the elastic portion 32 and a second side of the elastic portion 32 are both spaced apart from an inner circumferential surface of the notch 34. When the height of the support member 1 needs to be reduced, the elastic portion 32 is pulled out of the notch 34, to facilitate the separation of the first matching portion 31 and the second matching portion 41. In the embodiments, a step surface is provided at the bottom of the cavity 331, and when the rotating body 4 is arranged in the cavity 331, the operation teeth 45 of the rotating body 4 can abut against the step surface. The position of the rotating body 4 in the cavity 331 can be limited by the step surface. Meanwhile, the elastic portion 32 and the base body 33 can be integrally formed, which can ensure the stability of the entire structure. Specifically, the elastic portion 32 is formed by cutting the base body 33 by wire-electrode cutting. In other embodiments, other processing methods can be adopted. Alternatively, the elastic portion 32 and the base body 33 are configured as separate structures.

In some embodiments, the second matching portion 41 includes a plurality of ratchets spaced apart from each other along the outer circumferential surface of the rotating body 4. The first matching portion 31 is a protrusion that may be located between two adjacent ratchets. When the rotating body 4 rotates clockwise or counterclockwise, the protrusion can slide over the ratchets and restrict the rotating body 4 from rotating in the opposite direction.

Specifically, as shown in FIGS. 6-9, the second matching portion 41 includes the plurality of ratchets spaced apart from each other along the outer circumferential surface of the rotating body 4, and the plurality of ratchets can rotate synchronously with the rotating body 4. The first matching portion 31 is the protrusion on an inner circumferential surface of the elastic portion 32. An inner circumferential surface of the protrusion extends clockwise and is inclined inward along the inner-outer direction. The protrusion may have a curved surface or a plat surface. When the height of the support member 1 needs to be increased, the plurality of ratchets rotate clockwise with the rotating body 4, and the protrusion can pass through a tooth space between two adjacent ratchets. When the rotating body 4 drives the plurality of ratchets to rotate by an angle, the ratchets can slide on a transition surface 311, so that the rotating body 4 can rotate smoothly. When the rotating body 4 rotates counterclockwise, a side surface of the protrusion will get stuck with the ratchets, preventing the rotating body 4 from rotating counterclockwise. When the height of the support member 1 needs to be reduced, the elastic portion 32 is pulled to drive the ratchets to disengage from the protrusion, so that the rotating body 4 can rotate counterclockwise. Alternatively, as shown in FIGS. 4 and 5, when the height of the support member 1 needs to be increased, the plurality of ratchets rotate counterclockwise with the rotating body 4, and the protrusion can pass through the tooth space between two adjacent ratchets. When the rotating body 4 drives the plurality of ratchets to rotate by an angle, the ratchets can slide on the transition surface 311, so that the rotating body 4 can rotate smoothly. When the rotating body 4 rotates clockwise, the side face of the protrusion will get stuck with the ratchets, preventing the rotating body 4 from rotating clockwise. When the height of the support member 1 needs to be reduced, the elastic portion 32 is pulled to drive the ratchets to disengage from the protrusion, so that the rotating body 4 can rotate clockwise.

In some embodiments, the artificial vertebral body 100 further includes a driver (not shown in the drawings) which passes through the elastic portion 32 and can drive the elastic portion 32 to move to separate the first matching portion 31 from the second matching portion 41. Specifically, the driver may be a pin shaft and inserted into the elastic portion 32, and the elastic portion 32 is driven away from the rotating body 4 through the driver, so that the first matching portion 31 and the second matching portion 41 are separated.

In some embodiments, the elastic portion 32 includes a through hole 321 penetrating the elastic portion 32, and the driver is fitted in the through hole 321 through threads. Specifically, as shown in FIGS. 8 and 11, the elastic portion 32 includes the through hole 321 penetrating the elastic portion 32 in the inner-outer direction, the driver has an external thread, and the elastic portion 32 has an internal thread fitted with the external thread, so that the driver is fixed on the elastic portion 32 through the fitting of the internal and external threads, avoiding the separation between the driver and the elastic portion, and ensuring the movement efficiency of the elastic portion 32 driven by the driver. In the embodiments, by rotating the driver, the driver abuts against the rotating body 4, and the driver continues to rotate, so that the elastic portion 32 is lifted away from the rotating body 4 due to the action of the rotating body 4, allowing the first matching portion 31 to separate from the second matching portion 41. Alternatively, the first matching portion 31 and the second matching portion 41 can also be separated directly by pulling the elastic portion 32 outward through the driver.

It can be understood that the driver and the through hole 321 can also be connected through clamped, interference fit or the like, and the through hole 321 and the operation hole 36 are corresponding to each other in the up-down direction. Specifically, the through hole 321 and the operation hole 36 are arranged corresponding to each other in the up-down direction, and during a vertebral body implantation process, a double-channel tube can be used for the implantation into the human body in such a way that its two channels are aligned with the through hole 321 and the operation hole 36 respectively, and then the operation handle 5 or the driver can be inserted into the double-channel tube, which can simplify the surgical process. Meanwhile, the through hole 321 may be configured as a full hole or may be configured to be larger than a half hole. In other embodiments, the through hole 321 and the operation hole 36 are staggered in the up-down direction.

In some embodiments, the housing 3 is provided with a limiting member that can cooperate with the rotating body 4 to limit the rotating body 4 from coming out of the housing 3 along the axial direction of the rotating body 4. Consequently, the limiting member and the step surface cooperate with the rotating body 4, so that the rotating body 4 can rotate clockwise or counterclockwise in the housing 3 while the rotating body 4 is restricted from moving in the up-down direction, preventing the rotating body 4 from slipping out of the housing 3, and ensuring the working efficiency of the rotating body 4.

In some embodiments, the limiting member is a pin shaft (not shown in the drawings), the outer circumferential surface of the rotating body 4 has a positioning groove 42 extending along its circumferential direction, and the pin shaft passes through the housing 3 and fits with the positioning groove 42 to limit the axial movement of the rotating body 4. Specifically, as shown in FIGS. 3-9, the outer circumferential side of the rotating body 4 is provided with an annular positioning groove 42, and an end of the pin shaft can pass through the housing 3 and be inserted into the positioning groove 42. Consequently, when the rotating body 4 rotates, due to the fit of the positioning groove 42 and the pin shaft, the rotating body 4 can smoothly rotate inside the housing 3 to prevent the rotating body 4 from moving in the up-down direction, thus ensuring that the rotating body 4 only rotates inside the housing 3 and preventing the rotating body 4 from moving up and down inside the housing 3.

Figure 10:
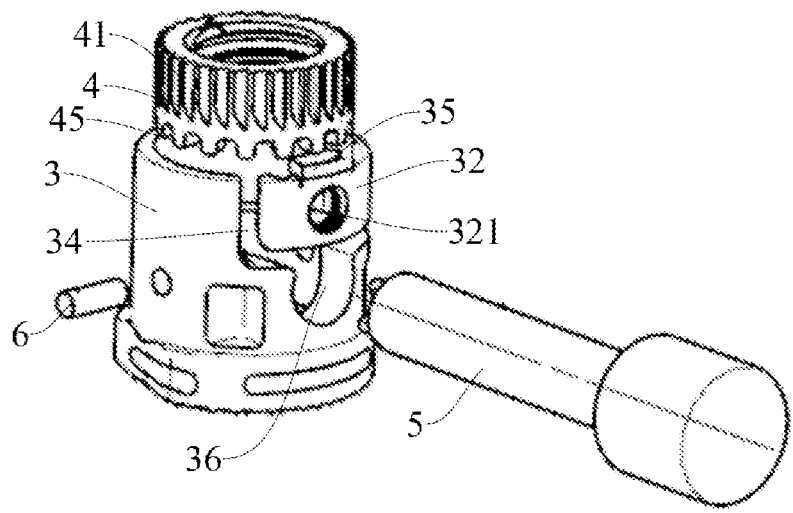
FIG. 10 is an exploded view of a rotating body and a housing of an artificial vertebral body according to a second embodiment of the present disclosure.

In other embodiments, the limiting member is a snap protrusion 35 at an end of the housing 3 adjacent to the rotating body 4, and the snap protrusion 35 extends inward in the radial direction of the rotating body 4, and abuts against an end of the rotating body 4 away from the housing 3 to limit the rotating body 4 from coming out of the housing 3 in the axial direction of the rotating body 4. Specifically, as shown in FIGS. 10-11, the snap protrusion 35 is arranged on the elastic portion 32, and the rotating body 4 can be confined in the cavity 331 through the cooperation of the snap protrusion 35 and the step surface. Since the snap protrusion 35 is arranged on the elastic portion 32, the elastic portion 32 can be pulled away through the driver when the rotating body 4 needs to be placed inside the housing 3, so that the snap protrusion 35 will not interfere; and the elastic portion 32 can be released after the rotating body 4 is placed, so that the snap protrusion 35 can limit the position of the rotating body 4, which eliminates the trouble of providing the positioning groove 42 on the rotating body 4, and is simple and convenient to operate.

In some embodiments, the housing 3 further includes a connection plate (not shown in the drawings) at the end of the housing 3 adjacent to the rotating body 4, and the snap protrusion 35 is formed on a side of the connection plate facing the rotating body 4. Specifically, the upper end of the housing 3 includes a mounting hole (not shown in the drawings), and the connection plate is arranged in the mounting hole, and the bottom of the connection plate is connected to the bottom of the mounting hole. The snap protrusion 35 is formed on an inner circumferential side of an upper end of the connection plate, and the snap protrusion 35 abuts against an upper end face of the rotating body 4. The connection plate can facilitate the mounting of the rotating body 4 inside the housing 3 and improve the mounting efficiency of the rotating body 4. Meanwhile, in the embodiments, it is unnecessary to mount the snap protrusion 35 on the elastic portion 32, and instead, the snap protrusion 35 can be mounted in the mounting hole through the connection plate after the rotating body 4 is positioned in the cavity 331.

In some embodiments, the outer circumferential side of the support member 1 is provided with a limiting groove 11 extending in the up-down direction, and an end of a pin 6 passes through the housing 3 and is inserted into the limiting groove 11, so that the rotation of the support member 1 is limited by the cooperation of the pin 6 and the limiting groove 11. Specifically, as shown in FIGS. 2 and 3, the outer circumferential side of the support member 1 includes the limiting groove 11 extending in the up-down direction, and one end of the pin 6 passes through the housing 3 and is inserted into the limiting groove 11, so that the rotation of the support member 1 is limited through the cooperation of the pin 6 and the groove 11, and the rotation of the rotating body 4 drives the support member 1 to move in the up-down direction.

In some embodiments, an end of the housing 3 away from the support member 1 and an end of the support member 1 away from the housing 3 are each provided with a plurality of convex portions 21. Specifically, the end of the housing 3 away from the support member 1 is provided with an endplate 2, and a plurality of convex portions 21 are provided at the bottom of the housing 3 and at the top of the endplate 2, in which the convex portions 21 are tapered in shape. Through the plurality of convex portions 21, the stability of the endplate 2 and the housing 3 at an initial stage of connection with human vertebrae can be enhanced, and the long-term fixation effect can be achieved after the human bone grows and is fully connected to the artificial vertebral body 100.

In other embodiments, the artificial vertebral body 100 further includes a first endplate and a second endplate (not shown in the drawings). The first endplate is detachably arranged at the end of the support member 1 away from the housing 3, and the second endplate is detachably arranged at the end of the housing 3 away from the support member 1. An end of the first endplate away from the support member 1 is a first end, and an end of the second endplate away from the housing 3 is a second end. Each of the first end and the second end is provided with the plurality of convex portions 21. Specifically, in the embodiments, the first endplate can be fixed at an upper end of the support member 1 by a fastener (not shown in the drawings) and an upper end of the first endplate is provided with the plurality of convex portions 21; and the second endplate can be fixed at a lower end of the housing 3 by a fastener (not shown in the drawings) and a lower end of the second endplate is provided with the plurality of convex portions 21. As a result, the first endplate and the second endplate with different shapes (rectangular or circular) can be replaced according to actual situations, so that the artificial vertebral body can adapt to different positions such as cervical vertebrae or thoracolumbar vertebrae, and the therapeutic effect of the artificial vertebral body 100 can be improved.

In the specification, it is to be understood that terms such as "central," "longitudinal," "transverse," "length," "width," "thickness," "up," "down," "front," "rear," "left," "right," "vertical," "horizontal," "top," "bottom," "inner," "outer," "clockwise," "counterclockwise," "axial," "radial" and "circumferential" should be construed to refer to the orientation as then described or as shown in the drawings under discussion. These relative terms are for convenience of description and do not require that the present disclosure have a particular orientation or be constructed and operated in a particular orientation. Thus, these terms shall not be construed as limitations on the present disclosure.

In addition, terms such as "first" and "second" are used herein for purposes of description and are not intended to indicate or imply relative importance or significance or to imply the number of indicated technical features. Thus, the feature defined with "first" and "second" may include one or more of this feature. In the description of the present disclosure, the term "a plurality of" means at least two, such as two or three, unless specified otherwise.

In the present disclosure, unless specified or limited otherwise, the terms "mounted," "connected," "coupled," "fixed" and the like are used broadly, and may be, for example, fixed connections, detachable connections, or integral connections; may also be mechanical or electrical connections; may also be direct connections or indirect connections via intervening structures; may also be inner communications or mutual interaction of two elements, which can be understood by those skilled in the art according to specific situations.

In the present disclosure, unless specified or limited otherwise, a structure in which a first feature is "on" or "below" a second feature may include an embodiment in which the first feature is in direct contact with the second feature, and may also include an embodiment in which the first feature and the second feature are not in direct contact with each other, but are contacted via an additional feature formed therebetween. Furthermore, a first feature "on," "above," or "on top of" a second feature may include an embodiment in which the first feature is right or obliquely "on," "above," or "on top of" the second feature, or just means that the first feature is at a height higher than that of the second feature; while a first feature "below," "under," or "on bottom of" a second feature may include an embodiment in which the first feature is right or obliquely "below," "under," or "on bottom of" the second feature, or just means that the first feature is at a height lower than that of the second feature.

Reference throughout this specification to "an embodiment," "some embodiments," "an example," "a specific example," or "some examples," means that a particular feature, structure, material, or characteristic described in connection with the embodiment or example is included in at least one embodiment or example of the present disclosure. Thus, the appearances of these phrases in various places throughout this specification are not necessarily referring to the same embodiment or example of the present disclosure. Furthermore, the particular features, structures, materials, or characteristics may be combined in any suitable manner in one or more embodiments or examples. In addition, different embodiments or examples as well as features in different embodiments or examples can be united and combined by those skilled in the art without mutual contradiction.

Although embodiments have been shown and described, it would be appreciated by those skilled in the art that the above embodiments are merely exemplary and cannot be construed to limit the present disclosure, and changes, modifications, alternatives and variations can be made in the embodiments without departing from the scope of the present disclosure.

What is claimed is:

1. An artificial vertebral body, comprising:
   a housing comprising a first matching portion on an inner circumferential surface of the housing;
   a rotating body rotatably arranged inside the housing and comprising a second matching portion on an outer circumferential surface of the rotating body, wherein the first matching portion is fitted with the second matching portion to limit the rotating body to only clockwise or counterclockwise rotation; and
   a support running through the rotating body and screwed with the rotating body, wherein the rotating body is rotatable relative to the housing to drive the support member to move along an axial direction of the rotating body.

2. The artificial vertebral body according to claim 1, wherein the housing comprises an elastic portion arranged corresponding to the rotating body in a radial direction of the rotating body, the first matching portion being formed on an inner side of the elastic portion, and the elastic portion drives the first matching portion to separate from the second matching portion.

3. The artificial vertebral body according to claim 2, wherein the housing comprises a base body and the elastic portion, the base body has a cavity, and the rotating body is rotatably arranged in the cavity;
   the base body comprises a notch at an end of the base body adjacent to the rotating body, and the elastic portion is arranged in the notch; and
   the elastic portion extends along a circumferential direction of the housing, and an end of the elastic portion in an extension direction is connected to the housing.

4. The artificial vertebral body according to claim 2, wherein:
   the second matching portion comprises a plurality of ratchets spaced apart from each other along the outer circumferential surface of the rotating body; and
   the first matching portion comprises a protrusion configured to be located between two adjacent ratchets, wherein in response to rotation of the rotating body in one of a clockwise direction and a counterclockwise direction, the protrusion slides over the ratchets and restricts the rotating body from rotating in the other of the clockwise direction and the counterclockwise direction.

5. The artificial vertebral body according to claim 2, further comprising a driver passing through the elastic portion and configured to drive the elastic portion to move to separate the first matching portion from the second matching portion.

6. The artificial vertebral body according to claim 5, wherein the elastic portion comprises a through hole penetrating the elastic portion, and the driver is fitted in the through hole by threads.

7. The artificial vertebral body according to claim 1, wherein the housing comprises a limiting member, and the limiting member cooperates with the rotating body to limit the rotating body from coming out of the housing along the axial direction of the rotating body.

8. The artificial vertebral body according to claim 7, wherein the limiting member comprises a pin shaft; the outer circumferential surface of the rotating body has a positioning groove extending along a circumferential direction of the rotating body; and the pin shaft passes through the housing and fits with the positioning groove to limit an axial movement of the rotating body.

9. The artificial vertebral body according to claim 7, wherein the limiting member comprises a snap protrusion at an end of the housing adjacent to the rotating body; the snap protrusion extends inward in a radial direction of the rotating body; and the snap protrusion abuts against an end of the rotating body away from the housing to limit the rotating body from coming out of the housing in the axial direction of the rotating body.

10. The artificial vertebral body according to claim 1, wherein each of an end of the housing away from the support member and an end of the support member away from the housing is provided with a plurality of convex portions.

11. The artificial vertebral body according to claim 1, further comprising a first endplate and a second endplate,
    wherein the first endplate is detachably arranged at an end of the support member away from the housing, and the second endplate is detachably arranged at an end of the housing away from the support member;
    an end of the first endplate away from the support member is a first end, an end of the second endplate away from the housing is a second end, and each of the first end and the second end is provided with the plurality of convex portions.

* * * * *